United States Patent [19]

Vincent et al.

[11] 4,104,437
[45] Aug. 1, 1978

[54] PRESSURE-SENSITIVE COPY SYSTEM INCLUDING UREIDO FLUORAN CHROMOGENIC COMPOUNDS

[75] Inventors: David N. Vincent, San Diego, Calif.; Cheng-Hsiung Chang, Naperville, Ill.

[73] Assignee: Champion International Corporation, Stamford, Conn.

[21] Appl. No.: 611,205

[22] Filed: Sep. 8, 1975

Related U.S. Application Data

[63] Continuation-in-part of Ser. No. 508,834, Sep. 24, 1974, abandoned.

[51] Int. Cl.² .................................................. B32B 3/26
[52] U.S. Cl. .................................... 428/307; 252/316; 260/335; 282/27.5; 427/151; 427/152; 428/327; 428/914
[58] Field of Search ................ 252/316; 428/307, 914, 428/327; 427/151, 152; 260/335, 96.5 R; 282/27.5

[56] References Cited

U.S. PATENT DOCUMENTS

| | | |
|---|---|---|
| 3,328,257 | 6/1967 | Vrancken et al. ............... 252/316 X |
| 3,576,660 | 4/1971 | Bayless et al. ................... 252/316 X |
| 3,649,649 | 3/1972 | Orita et al. ....................... 252/316 X |
| 3,669,711 | 6/1972 | Kimura et al. ........................ 428/307 |
| 3,703,397 | 11/1972 | Lin et al. .............................. 282/27.5 |
| 3,715,226 | 2/1973 | Lin ....................................... 282/27.5 |
| 3,721,576 | 3/1973 | Farber et al. ........................ 282/27.5 |
| 3,730,755 | 5/1973 | Lin ....................................... 282/27.5 |

*Primary Examiner*—Richard D. Lovering
*Attorney, Agent, or Firm*—Roylance, Abrams, Berdo & Farley

[57] ABSTRACT

A chromogenic compound having the structural formula

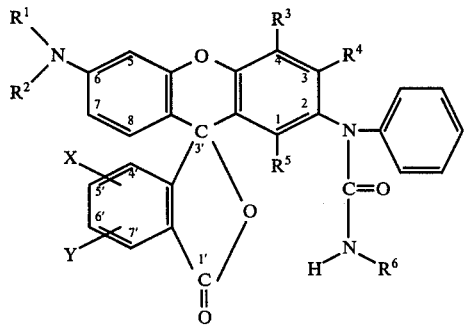

wherein
$R^1$ and $R^2$ each represent an alkyl group;
$R^3$ and $R^4$ each represent a hydrogen atom, a halogen atom, an alkyl group, a nitro group, an amino group, an acyl group, or a carboalkoxy group;
$R^5$ represents a hydrogen atom or an alkyl group, with the proviso that $R^5$ represents an alkyl group only when $R^4$ represents a hydrogen atom;
$R^6$ represents an alkyl group, an aryl group or an aralkyl group; and
X and Y each represent a hydrogen atom, a halogen atom, a nitro group, a lower alkyl group, an aryl group, an alkoxy group or a carboalkoxy group.

The aforesaid compound may be provided in a pressure-sensitive copy system wherein a visible image is formed upon reaction of the above chromogenic compound with an electron-accepting material of the Lewis acid type.

10 Claims, No Drawings

PRESSURE-SENSITIVE COPY SYSTEM INCLUDING UREIDO FLUORAN CHROMOGENIC COMPOUNDS

This application is a continuation-in-part of U.S. application Ser. No. 508,834 filed Sept. 24, 1974, and now abandoned, in the name of D. N. Vincent and C. H. Chang.

This invention relates to chromogenic compounds, the production of such compounds, and to pressure-sensitive copy systems employing such compounds. More particularly, this invention relates to substantially colorless substituted ureido fluoran chromogenic compounds which are converted to a visible red image when placed in reactive contact with a Lewis acid material, such as acid clay, the production of such compounds, and to pressure-sensitive copy systems wherein such compounds are enclosed in microcapsules.

Numerous marking systems have been suggested which involve localized contact between a chromogenic compound and a color-developing substance in areas where a colored marking is desired. Pressure-sensitive mark-forming systems are described, for example, in U.S. Pat. Nos. 3,418,656 and 3,418,250 to A. E. Vassiliades. These patents describe a marking system wherein a substantially colorless chromogenic substance is disposed in minute oil droplets within microcapsules, the walls of which form pressure-rupturable barriers. The microcapsules are coated onto a substrate which is superimposed onto a receiving sheet, which is coated with an electron-accepting material of the Lewis acid type, such as an acid-treated clay. Upon application of localized pressure to the opposite side of the microcapsule-coated sheet, the microcapsules are ruptured and the colorless chromogenic substance is released for reaction with the acidic co-reactant to provide a distinctive mark.

Various fluoran chromogenic compounds have been proposed for use in such marking systems. However, certain deficiencies have been encountered. For example, some fluoran chromogenic compounds lack stability upon exposure to light. Likewise, other chromogenic substances do not form images that are readily reproducible by xerographic or other reproductive processes.

In accordance with the present invention, substantially colorless, chromogenic compounds capable of providing a visible coloration are provided, said compounds having the structural formula

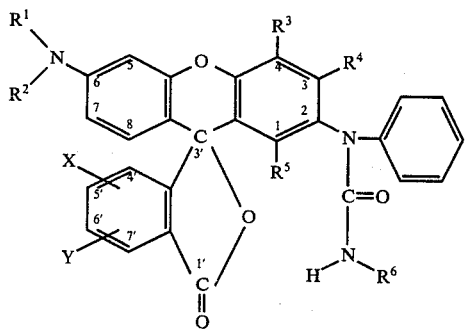

wherein
$R^1$ and $R^2$ each represent an alkyl group;

$R^3$ and $R^4$ each represent a hydrogen atom, a halogen atom, an alkyl group, a nitro group, an amino group, an acyl group, or a carboalkoxy group;

$R^5$ represents a hydrogen atom or an alkyl group, with the proviso that $R^5$ represents an alkyl group only when $R^4$ represents a hydrogen atom;

$R^6$ represents an alkyl group, an aryl group or an aralkyl group; and

X and Y each represent a hydrogen atom, a halogen atom, a nitro group, a lower alkyl group, an aryl group, an alkoxy group or a carboalkoxy group.

The substantially colorless ureido fluoran chromogenic compounds of the present invention are converted to a red coloration upon contact with an acidic color-reacting substance, e.g., a Lewis acid material such as acid clay, a phenolic resin, or a carboxylic acid of the type described in U.S. Pat. No. 3,488,207 to Vassiliades. Significantly, the red markings provided by the chromogenic compounds of the present invention possess excellent stability upon exposure to light.

Preferably the ureido fluorans of the present invention have the structural formula set forth above wherein:

$R^1$ and $R^2$ each represent a lower alkyl group having 1 to 4 carbon atoms, e.g., methyl, ethyl, propyl, butyl;

$R^3$ and $R^4$ each represent a hydrogen atom, a halogen atom, e.g., chlorine, bromine, etc., a lower alkyl group, e.g., methyl, ethyl, propyl, etc., a nitro group, a primary amino group, a $C_2$–$C_5$ acyl group, e.g. acetyl, butyryl, etc., or a lower carboalkoxy group, i.e., carbomethoxy, carboethoxy, carbopentoxy group;

$R^5$ represents a hydrogen atom or a lower alkyl group, with the proviso that $R^5$ represents an alkyl group only when $R^4$ represents a hydrogen atom; and $R^6$ represents a lower alkyl group having from 1 to 4 carbon atoms, e.g. methyl, ethyl, propyl, butyl group; an aryl group, e.g. phenyl, 4-methyl phenyl, 4-chlorophenyl, naphthyl, etc., or an aralkyl group, e.g. benzyl, etc.

X and Y each represent a hydrogen atom, a halogen atom, e.g., chlorine, fluorine, bromine, iodine, a nitro group, a lower alkyl group having 1 to 5 carbon atoms, e.g., methyl, ethyl, propyl, butyl, amyl, an aryl group, e.g., phenyl, 4-methyl phenyl, 4-chloro-phenyl, naphthyl, etc.; a lower alkoxy group, e.g., methoxy, ethoxy, pentoxy group; a lower carboalkoxy group, e.g., carbomethoxy, carboethoxy, carbopentoxy group, etc.

Especially preferred ureido fluorans of the present invention have the above structural formula wherein
$R^1$ and $R^2$ each represent a lower alkyl group having from 1 to 4 carbon atoms;

$R^3$ and $R^4$ each represent a hydrogen atom, a methyl group or a halogen atom;

$R^5$ represents a hydrogen atom or a methyl group, with the proviso that $R^5$ represents a methyl group only when $R^4$ represents a hydrogen atom;

$R^6$ represents a lower alkyl group having from 1 to 4 carbon atoms, an aryl group, or an aralkyl group; and X and Y each represent a hydrogen atom or a chlorine atom.

Another group of preferred ureido fluorans are those having the structural formula above wherein $R^5$, X and Y represent a hydrogen atom, and $R^1$–$R^6$ are defined as above.

Examples of the ureido fluorans of the present invention include:
2-(N'-phenyl-N-phenylureido)-6-diethylaminofluoran;

2-(N'-phenyl-N-phenylureido)-3-methyl-6-diethylaminofluoran;
2-(N'-phenyl-N-phenylureido)-1-methyl-6-diethylaminofluoran;
2-(N'-phenyl-N-phenylureido)-3-chloro-6-diethylaminofluoran;
2-(N'-phenyl-N-phenylureido)-3-methyl-4-ethyl-6-diethylaminofluoran;
2-(N'-methyl-N-phenylureido)-6-diethylaminofluoran;
2-(N'-ethyl-N-phenylureido)-6-diethylaminofluoran;
2-(N'-benzyl-N-phenylureido)-6-diethylaminofluoran;
2-(N'-naphthyl-N-phenylureido)-6-diethylaminofluoran;
2-(N'phenyl-N-phenylureido)-4-chloro-6-diethylaminofluoran;
2-(N'-ethyl-N-phenylureido)-3-bromo-6-diethylaminofluoran;
2-(N'-phenyl-N-phenylureido)-3-acetyl-6-diethylaminofluoran;
2-(N'-phenyl-N-phenylureido)-4-carbomethoxy-6diethylaminofluoran;
2-(N'-phenyl-N-phenylureido)-3-nitro-6diethylaminofluoran;
2-(N'-butyl-N-phenylureido)-6-diethylaminofluoran;
5', 7'-dichloro-2-(N'-phenyl-N-phenylureido)-6diethylaminofluoran;
4', 6'-dichloro-2-(N'-phenyl-N-phenylureido)-6-diethylaminofluoran;
5', 7'-dinitro-2-(N'-phenyl-N-phenylureido)-6diethylaminofluoran;
4', 5'-dimethyl-2-(N'-phenyl-N-phenylureido)-6-diethylaminofluoran;
5', 7'-diphenyl-2-(N'-phenyl-N-phenylureido)-6-diethylaminofluoran;
6', 7'-dimethoxy-2-(N'-phenyl-N-phenylureido)-6-diethylaminofluoran;
5', 7'-dicarboethoxy-2(N'-phenyl-N-phenylureido)-6-diethylaminofluoran;
5'-chloro, 7'-methyl-2-(N'-phenyl-N-phenylureido)-6-diethylaminofluoran; and the like.

According to the present invention, the ureido fluorans of the present invention are produced by reacting phthalic anhydride with a dialkylamino phenol to produce 2'-carboxy-4-dialkylamino-2-hydroxybenzophenone as follows:

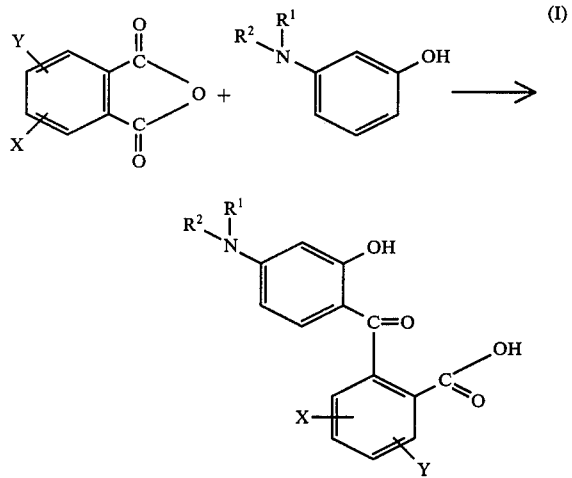

Next, the resulting compound is reacted with a p-anilinophenol to produce the precursor fluoran compound as follows:

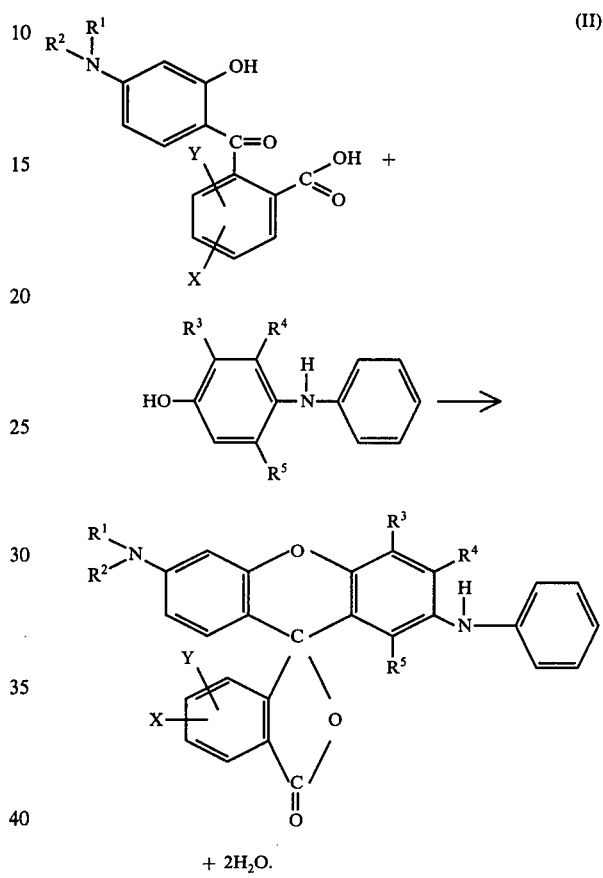

According to another aspect of the present invention, the resulting precursor fluoran compound is then reacted with an isocyanate to produce the compound of the present invention as follows:

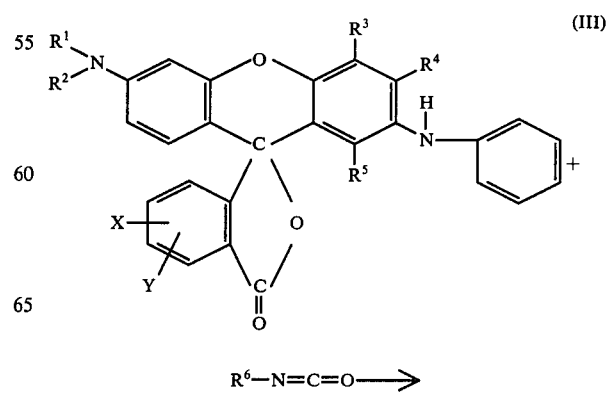

-continued

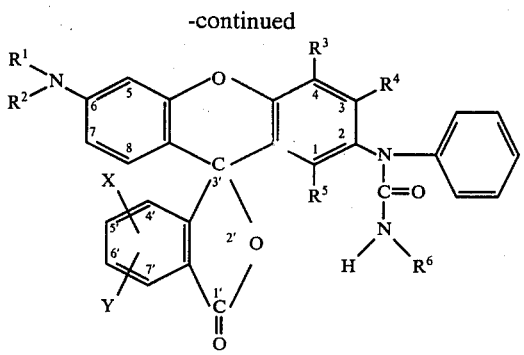

Reaction II is conducted under acidic conditions, e.g., in the presence of sulfuric or phosphoric acid, at a temperature, for example, in the range of between about 10° and about 60° C., preferably between about 20° and about 40° C., under atmospheric pressure conditions, for a period of, for example, between about 2 and about 80 hours, preferably between about 6 and about 65 hours. In the foregoing reactions, $R^1$, $R^2$, $R^3$, $R^4$, $R^5$, $R^6$, X and Y are defined as previously indicated. Accordingly, the isocyanate employed in Reaction III may be any isocyanate having the formula $R^6$—N=C=O, such as methyl isocyanate, ethyl isocyanate, t-butyl isocyanate, α-naphthylisocyanate, phenyl isocyanate, benzyl isocyanate, 4-chlorophenyl isocyanate, and the like. Reaction III is conducted, for example, at a temperature in the range of between about 40° and about 150° C. for a period of between about 2 and 10 hours.

The reaction product of the present invention formed in Reaction III is washed with water, precipitated out in heptane, and dried to produce a substantially colorless solid product which becomes red in color upon contact with a Lewis acid material.

Moreover, a predetermined quantity of isocyanate may be used to react with precursor fluoran compounds, forming a mixture of some unreacted precursor and the corresponding ureido derivative. The combination of precursor and ureido derivative at a molar ratio of, for example, in the range of between about 0.2 and about 0.9 mole of ureido derivative per mole of precursor, preferably between about 0.5 and about 0.8 mole per mole, provides an intense black image upon reaction with a Lewis acid material, such as an acid-treated clay. The particular ratio utilized depends upon the nature of the Lewis acid material. The employment of temperatures in the range of 40° to 60° C. and reaction times of 2 to 4 hours for Reaction III permits the production of appropriate ratios of ureido derivative to precursor to yield a black-yielding chromogen. The resulting black images have excellent color stability upon exposure to light and heat. More importantly, the black images developed on the copy down-to-the-form, i.e. the last copy, are very legible compared to those of the conventional blue imaging system and can be clearly reproduced by xerographic machines.

According to a further aspect of the present invention, the ureido fluorans of the present invention may be dissolved in an oily solvent, such as a dialkylnaphthalene, cottonseed oil, coconut oil, a chlorinated biphenyl, or the like, and encapsulated for use in a carbonless copy system.

Any suitable process may be utilized for forming the microcapsules and the copy sheets bearing such microcapsules including those processes described in U.S. Pat. Nos. 3,418,250 and 3,418,656, the disclosures of which are hereby incorporated by reference. The resultant microcapsules may be coated on or incorporated in a web or substrate, such as paper, and utilized in any form of pressure-sensitive copy system wherein the microcapsules are ruptured under localized pressure to release the ureido fluoran for contact with an acidic co-reactant. Thus, for example, the microcapsule-bearing substrate may be also coated with the acidic, co-reactant, such as an acidic clay. Such system is normally referred to as a "self-contained" or "autogenous" system, since the colorless chromogenic material and the acidic, co-reactant are present on the same substrate.

Alternatively, the microcapsules containing the fluorans of the present invention may be coated onto and/or incorporated into a substrate which is used in combination with a separate sheet or substrate which contains the acidic co-reactant. This type of copy system is normally referred to as a "transfer copy system", and upon rupture of the capsules by localized pressure the fluoran chromogen contacts a separate acid-coated sheet upon which a colored mark is thereby provided. Accordingly, the colorless fluorans of the present invention may be utilized in any copy system where they are isolated from the acidic co-reactant prior to the formation of the desired colored image.

According to another aspect of the present invention, the fluoran chromogenic compounds of the present invention are employed in pressure-rupturable copy systems wherein the fluoran compounds are enclosed in microcapsules that are formed by a reaction involving a poly-functional isocyanate. The preferred system for forming microcapsules involving the fluoran compounds of the present invention is described in U.S. Pat. No. 3,875,074 to A. E. Vassiliades et al, the disclosure of which is hereby incorporated by reference. According to the system described therein, pressure-rupturable oil-containing microcapsules are provided by admixing:

(A) A water-immiscible, oily material containing the fluoran compound of the present invention and an oil-soluble, non-polymeric cross-linking agent in the form of a poly-functional isocyanate; and (B) An aqueous solution of an organic, polymeric emulsifying agent containing a plurality of hydroxyl groups. The water-immiscible oily material and the aqueous solution of the emulsifying agent are admixed under conditions to form an oil-in-water emulsion, wherein the oily material is dispersed in the form of microscopic emulsion droplets in an aqueous, continuous phase. The emulsifying agent aids in the formation of the emulsion and additionally, possesses cross-linkable hydroxyl groups that are capable of reacting with the cross-linking agent to form a cross-linked capsule wall at the oil/water interface. The cross-linking agent is reacted with the hydroxyl groups of the polymeric emulsifying agent and in such manner surrounds each of the droplets with a solid, cross-linked capsule wall.

The preferred oil-soluble poly-functional isocyanates are 4,4'-diphenylmethane diisocyanate, toluene diisocyanate, hexamethylene diisocyanate, triphenylmethane triisocyanate, mixtures of such isocyanates, and adducts of such isocyanates with polyhydric alcohols, such as trimethylolpropane. A preferred isocyanate cross-linking agent is an adduct of toluene diisocyanate with glycerol (3:1 molar), pentaerythritol (4:1 molar), hexanetriol (3:1 molar) or trimethylolpropane (3:1 molar).

An especially preferred isocyanate cross-linking agent is the adduct of toluene diisocyanate and trimethylol propane.

The film-forming polymeric emulsifying agent may be a poly-hydroxyl group-containing polymer, such as polyvinyl alcohol, methylcellulose, a benzylated starch or the like.

As previously indicated, the dialkylamino fluorans of the present invention provide a red color upon contact with the electron-accepting Lewis acid material. Any of the well-known acidic materials including bentonite, kaolin, acidic clays, talc, aluminum silicate, calcium citrate, metal oxides, metal chlorides or the like.

Various concentrations of the present fluorans may be utilized in the formation of ureido fluoran-containing microcapsules for use in copy systems. Thus, for example, the fluorans can be used in amounts of between about 1 and about 6 parts by weight per 100 parts by weight of the oily core material of the microcapsules. Preferably, between about 2 and about 4 parts by weight per 100 parts by weight of oil may be used. Larger amounts of the fluoran may be utilized, if desired. However, relatively small amounts of the fluorans develop a high intensity color. Suitable amounts of the dialkylamino fluoran may be easily determined experimentally for each particular system.

The ureido fluorans of the present invention may also be used in combination with other colorless chromogenic compounds. For example, the precursor fluoran compound mentioned before, crystal violet lactone (CVL), and benzoyl leuco methylene blue (BLMB) may be added to provide an excellent black imaging system. The total quantity of the dyes per 100 parts by weight of the oily core material of the microcapsules can be in amounts of between about 2 and 8 parts by weight, while the molar ratio of ureido fluoran: precursor fluoran: CVL: BLMB: can be, for example, 2.0: 3.0: 0.1: 0.2. Preferably, between about 4 and 6 parts by weight per 100 parts by weight of oil may be used.

The invention will be further illustrated by the following examples. The percentages are by weight unless otherwise specified.

EXAMPLE I

Production of 2-anilino-6-diethylaminofluoran

Into 500 grams of 97% sulfuric acid and dissolved 31.3 grams of 2'-carboxy-4-diethylamino-2-hydroxy-benzophenone at room temperature. The solution is cooled to 10° C. and 18.5 grams of 4-anilinophenol are slowly added. The solution is then stirred at 20° C. for 65 hours to provide a reaction mixture containing a sulfate of 2-anilino-6-diethylaminofluoran.

EXAMPLE II

Preparation of
2-(N'-phenyl-N-phenylureido)-6-diethylaminofluoran-precursor mixture The reaction mixture of Example I is poured into 2000 grams of ice-water, basified to pH 9 with 20% sodium hydroxide solution, and extracted with xylene. The xylene solution is washed with 5% sodium hydroxide until the aqueous layer is nearly clear and finally with water three times. After concentrating to 300 ml, 11.9 grams of phenyl isocyanate are added.

The solution is heated at 60° C. for 2 hours, and subsequently, 100 ml of water are added while the stirring is continued for one hour. The organic phase is separated, dried over anhydrous sodium sulfate, and poured into 900 ml of heptane to precipitate 43.6 grams of the product, 2-(N'-phenyl-N-phenylureido)-6-diethylaminofluoran and its 2-anilino-6-diethylaminofluoran precursor.

EXAMPLE III

The procedure of Example II is repeated with the exception that methyl isocyanate, ethyl isocyanate, t-butyl isocyanate, and α-naphthylisocyanate, respectively, are substituted for phenyl isocyanate on a molar basis.

In such cases the precipitated product is a mixture of 2-anilino-6-diethylamino fluoran and its ureido derivative 2-(N'-methyl-N-phenylureido)-6-diethylaminofluoran; 2-(N'-ethyl-N-phenylureido)-6-diethylaminofluoran; 2-(N'-t-butyl-N-phenyl-ureido)-6-diethylaminofluoran; and 2-(N'-α-naphthyl-N-phenyl-ureido)-6-diethylaminofluoran, respectively.

EXAMPLE IV

The procedure of Examples I and II is repeated with the exception that 2-methyl-4-hydroxy-diphenylamine, 2-chloro-4-hydroxy-diphenylamine, and 3-carbomethoxy-4-hydroxy-diphenylamine are each substituted for the 4-anilinophenol. The resulting products are 2-(N'-phenyl-N-phenylureido)-3-methyl-6-diethylaminofluoran and its isomer, 2-(N'-pheny-N-phenylureido)-1-methyl-6-diethylaminofluoran; 2-(N'phenyl-N-phenylureido)-3-chloro-6-diethylaminofluoran; and 2-(N'-phenyl-N-phenylureido)-4-carbomethoxy-6-diethylaminofluoran, respectively, each in combination with the precursor 2-anilino-3 -methyl-6-diethylaminofluoran, 2-anilino-3chloro-6-diethylaminofluoran, and 2-anilino-4-carbomethoxy-6-diethylaminofluoran, respectively.

EXAMPLE V

Six parts of a toluene diisocyanate adduct of hexanetriol (3:1 molar, 75% solids, Mondur CB-75 from Mobay Chemical Company) are added to a dye solution of 5 parts of 2-(N'-phenyl-N-phenylureido)-6-diethylaminofluoran and its precursor 2-anilino-6-diethylaminofluoran in 100 parts of monoisopropylnaphthalene.

The solution is then emulsified in 214 parts of a 7% polyvinyl alcohol (87 to 89% hydrolyzed) aqueous solution. The emulsion is cured at 60° C. for 2 hours to complete the encapsulation.

The resulting microcapsules are coated onto a sheet of paper to form one part (the CB sheet) of a pressure-rupturable transfer system. The second part of the system is a receiving sheet (CF sheet) coated with acidic clay. Rupture of the microcapsules by a stylus pressure releases the dye intermediate solution which is absorbed onto the receiving sheet, producing an intense black image.

EXAMPLE VI

Preparation of
2-(N'-phenyl-N-phenylureido)-6-diethylaminofluoran

The reaction mixture of Example I is poured into 2000 grams of ice-water, basified to pH 9 with 20% sodium hydroxide solution, and extracted with xylene. The xylene solution is washed with 5% sodium hydroxide until the aqueous layer is nearly clear and finally with water three times. After concentrating to 300 ml, 11.9 grams of phenyl isocyanate are added.

The solution is refluxed at 145° C. for 4 hours and subsequently, 100 ml of water are added while the stirring is continued for one hour. The organic phase is separated, dried over anhydrous sodium sulfate, and poured into 900 ml of heptane to precipitate 51.6 grams of the product, 2-(N'-phenyl-N-phenyl-ureido)-6-diethylaminofluoran, having a melting point of 129°–131° C.

EXAMPLE VII

The procedure of Example VI is repeated with the exception that methyl isocyanate, ethyl isocyanate, t-butyl isocyanate, and α-naphthylisocyanate, respectively, are substituted for phenyl isocyanate on a molar basis.

In such cases the precipitated product is 2-(N'-methyl-N-phenylureido)-6-diethylaminofluoran; 2-(N'-ethyl-N-phenylureido)-6-diethylaminofluoran; 2-(N'-t-butyl-N-phenylureido)-6-diethylaminofluoran; and 2-(N'-α-naphthyl-N-phenylureido)-6-diethylaminofluoran, respectively.

EXAMPLE VIII

The procedure of Example VI is repeated with the exception that 2-methyl-4-hydroxy-diphenylamine, 2-chloro-4-hydroxy-diphenylamine, and 3-carbomethoxy-4-hydroxy-diphenylamine are substituted for 4-anilinophenol. The resulting product is
2-(N'-phenyl-N-phenylureido)-3-methyl-6-diethylaminofluoran;
2-(N'-phenyl-N-phenylureido)-3-chloro-6-diethylaminofluoran; and
2-(N'-phenyl-N-phenylureido)-4-carbomethoxy-6-diethylaminofluoran,
respectively.

EXAMPLE IX

Preparation of 5', 7'-dichloro-2-(N'-phenyl-N-phenylureido-6-diethylaminofluoran Into 500 grams of 97% sulfuric acid are dissolved 38.3 grams of 2'-carboxy-3', 5'-dichloro-4-diethylamino-2-hydroxybenzophenone at room temperature. The solution is cooled to 10° C. and 18.5 grams of 4-anilinophenol are slowly added. The solution is then stirred at 20° C. for 65 hours to provide a reaction mixture containing the sulfate of 5', 7'-dichloro-2-anilino-6-diethylaminofluoran. The resulting reaction mixture is poured into 2000 grams of icewater, basified to pH 9 with 20% sodium hydroxide solution, and extracted with xylene. The xylene solution is washed with 5% sodium hydroxide until the aqueous layer is nearly clear and finally with water three times. After concentrating to 300 ml, 11.9 grams of phenyl isocyanate are added.

The solution is refluxed at 145° C. for 4 hours, and subsequently, 100 ml of water are added while the stirring is continued for one hour. The organic phase is separated, dried over anhydrous sodium sulfate, and poured into 900 ml of heptane to precipitate 48.0 grams of the product, 5', 7'-dichloro-2-(N'-phenyl-N-phenylureido)-6-diethylaminofluoran.

EXAMPLE X

A dye solution of 2 parts of 5', 7'-dichloro-2-(N'-phenyl-N-phenylureido)-6-diethylaminofluoran in 100 parts of mono-isopropylnaphthalene are added 6 parts of a toluene diisocyanate adduct of hexanetriol (3:1 molar, 75% solids, Mondur CB-75 commercially available from Mobay Chemical Company).

The solution is then emulsified in 214 parts of a 7% polyvinyl alcohol (87 to 89% hydrolyzed) aqueous solution. The emulsion is cured at 60° C. for 2 hours to complete the encapsulation.

The resulting microcapsules are coated onto a sheet of paper to form one part (the CB sheet) of a pressure-rupturable transfer system. The second part of the system is a receiving sheet (CF sheet) coated with acidic clay. Rupture of the microcapsules by a stylus pressure releases the dye intermediate solution which is absorbed onto the receiving sheet, producing an intense red image.

EXAMPLE XI

To a dye solution of 2 parts of 2-(N'-phenyl-N-phenylureido)-6-diethylaminofluoran in 100 parts of mono-isopropylnaphthalene are added 6 parts of a toluene diisocyanate adduct of hexanetriol (3:1 molar, 75% solids, Mondur CB-75 commercially available from Mobay Chemical Company).

The solution is then emulsified in 214 parts of a 7% polyvinyl alcohol (87 to 89% hydrolyzed) aqueous solution. The emulsion is cured at 60° C. for 2 hours to complete the encapsulation.

The resulting microcapsules are coated onto a sheet of paper to form one part (the CB sheet) of a pressure-rupturable transfer system. The second part of the system is a receiving sheet (CF sheet) coated with acidic clay. Rupture of the microcapsules by a stylus pressure releases the dye intermediate solution which is absorbed onto the receiving sheet, producing an intense red image.

EXAMPLE XII

To a dye solution of 2.0 parts of 2-(N'-phenyl-N-phenylureido)-6-diethylaminofluoran, 3 parts of 2-anilino-6-diethylaminofluoran, 0.1 part of a crystal violet lactone and 0.2 part of benzoyl leuco methylene blue in 100 parts of mono-isopropylnaphthalene are added 6 parts of a toluene diisocyanate adduct of hexanetriol (3:1 molar, 75% solids, Mondur CB-75).

The procedure of Example XI is followed to encapsulate the dye solution and prepare a pressure-sensitive copying system. Rupture of the microcapsules produces an intense black image on the receiving sheet.

EXAMPLE XIII

To a dye solution of 1.6 parts of 2-(N'-phenyl-N-phenylureido)-6-diethylaminofluoran, 3.5 parts crystal violet lactone and 1.8 parts of benzoyl leuco methylene blue in 100 parts of mono-isopropylnaphthalene are added 6 parts of a toluene diisocyanate adduct of hexanetriol (3:1 molar, 75% solids, Mondur CB-75). The procedure of Example XI is followed to encapsulate the dye solution and prepare a pressure sensitive copying system. Rupture of the microcapsules produces an intense royal blue image on the receiving sheet.

This invention has been described in considerable detail with particular reference to preferred embodiments, but it will be understood that variations and modifications can be effected within the spirit and scope of the invention as described in the appended claims.

What is claimed is:

1. A pressure-sensitive copy system comprising a substrate bearing pressure-rupturable microcapsules containing a chromogenic compound having the formula

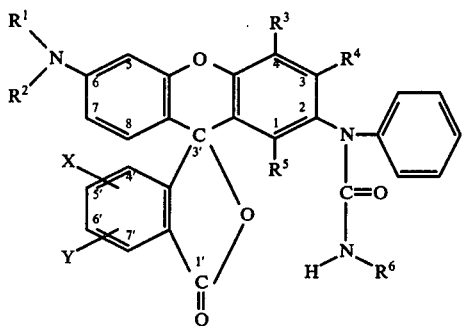

wherein
- $R^1$ and $R^2$ each represent an alkyl group;
- $R^3$ and $R^4$ each represent a hydrogen atom; a halogen atom, an alkyl group, a nitro group, an amino group, an acyl group, or a carboalkoxy group;
- $R^5$ represents a hydrogen atom or an alkyl group, with the proviso that $R^5$ represents an alkyl group only when $R^4$ represents a hydrogen atom;
- $R^6$ represents an alkyl group, an aryl group or an aralkyl group; and
- X and Y each represent a hydrogen atom, a halogen atom, a nitro group, a lower alkyl group, an aryl group, an alkoxy group, or a carboalkoxy group.

2. The pressure-sensitive copy system of claim 1 wherein
- $R^1$ and $R^2$ each represent a lower alkyl group having from 1 to 4 carbon atoms;
- $R^3$ and $R^4$ each represent a hydrogen atom, a methyl group or a halogen atom;
- $R^5$ represents a hydrogen atom or a lower alkyl group, with the proviso that $R^5$ represents an alkyl group only when $R^4$ represents a hydrogen atom;
- $R^6$ represents a lower alkyl group having from 1 to 4 carbon atoms, an aryl group, or an aralkyl group; and
- X and Y each represent hydrogen or a chlorine atom.

3. The pressure-sensitive copy system of claim 2 wherein said microcapsules additionally contain 2-anilino-6-diethylaminofluoran.

4. The pressure-sensitive copy system of claim 1 wherein $R^1$ and $R^2$ represent an ethyl group, $R^3$, $R^4$, $R^5$, X and Y represent hydrogen and $R^6$ represents a phenyl group, said compound being 2-(N'-phenyl-N-phenylureido)-6-diethylaminofluoran.

5. The pressure-sensitive copy system of claim 1 wherein $R^1$ and $R^2$ represent an ethyl group, $R^3$, $R^5$, X and Y represent hydrogen, $R^4$ represents a methyl group and $R^6$ represents a phenyl group, said compound being 2-(N'-phenyl-N-phenylureido)-3-methyl-6-diethylaminofluoran.

6. The pressure-sensitive copy system of claim 1 wherein said microcapsules additionally contain a chromogenic precursor having the formula

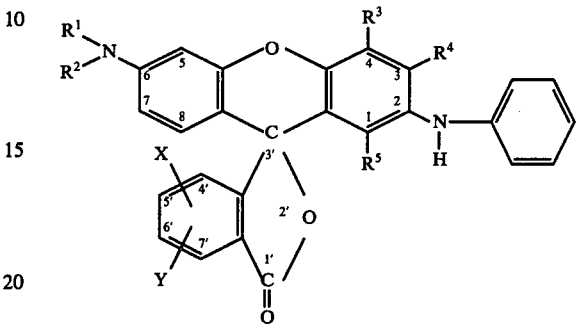

wherein
- $R^1$ and $R^2$ each represent an alkyl group;
- $R^3$ and $R^4$ each represent a hydrogen atom, a halogen atom, an alkyl group, a nitro group, an amino group, an acyl group, or a carboalkoxy group;
- $R^5$ represents a hydrogen atom or an alkyl group, with the proviso that $R^5$ represents an alkyl group only when $R^4$ represents a hydrogen atom;
- X and Y each represent a hydrogen atom, a halogen atom, a nitro group, a lower alkyl group, an aryl group, an alkoxy group, or a carboalkoxy group; and
- said chromogen and said chromogen precursor providing a black-image forming chromogenic admixture.

7. The pressure-sensitive copy system of claim 6 wherein the ratio of chromogen to chromogen precursor is between about 0.2 and about 0.9 mole of chromogen per mole of chromogen precursor.

8. The copy system of claim 1 wherein said microcapsules have walls formed by the reaction of a poly-functional isocyanate and an organic, polymeric emulsifying agent containing a plurality of hydroxyl groups.

9. the copy system of claim 8 wherein said isocyanate is an adduct of toluene diisocyanate and trimethylolpropane.

10. The copy system of claim 9 wherein said emulsifying agent is polyvinyl alcohol.

* * * * *